United States Patent
Learmonth et al.

(10) Patent No.: US 9,677,935 B2
(45) Date of Patent: Jun. 13, 2017

(54) FABRY-PEROT SPECTRAL IMAGE MEASUREMENT

(71) Applicant: TruTag Technologies, Inc., Kapolei, HI (US)

(72) Inventors: Timothy Learmonth, Berkeley, CA (US); Hod Finkelstein, El Cerrito, CA (US)

(73) Assignee: TruTag Technologies, Inc., Kapolei, HI (US)

( * ) Notice: Subject to any disclaimer, the term of this patent is extended or adjusted under 35 U.S.C. 154(b) by 0 days.

(21) Appl. No.: 14/581,935

(22) Filed: Dec. 23, 2014

(65) Prior Publication Data

US 2016/0123809 A1 May 5, 2016

Related U.S. Application Data

(60) Provisional application No. 62/074,455, filed on Nov. 3, 2014.

(51) Int. Cl.
| | |
|---|---|
| *G01J 3/45* | (2006.01) |
| *G01J 3/26* | (2006.01) |
| *G01J 3/02* | (2006.01) |
| *G01N 21/25* | (2006.01) |
| *G01J 3/10* | (2006.01) |

(52) U.S. Cl.
CPC ............... *G01J 3/26* (2013.01); *G01J 3/0237* (2013.01); *G01J 3/10* (2013.01); *G01N 21/255* (2013.01); *G01J 2003/102* (2013.01); *G01N 2201/061* (2013.01)

(58) Field of Classification Search
CPC .. G01J 3/26; G01J 3/0237; G01J 3/45; G01N 21/255; G01N 2201/061; C12Q 2565/514; C12Q 2563/149; C12Q 2563/155

USPC ......................................................... 356/454
See application file for complete search history.

(56) References Cited

U.S. PATENT DOCUMENTS

| | | | |
|---|---|---|---|
| 7,242,509 B2 | 7/2007 | Atia et al. | |
| 2005/0244096 A1* | 11/2005 | Jeffers | G01B 9/02007 385/15 |
| 2009/0323056 A1 | 12/2009 | Yun et al. | |
| 2011/0244588 A1 | 10/2011 | Maity et al. | |
| 2011/0303746 A1* | 12/2011 | Learmonth | G01N 21/3563 235/380 |
| 2014/0340671 A1* | 11/2014 | Xiao | G01N 22/00 356/72 |

* cited by examiner

*Primary Examiner* — Tarifur Chowdhury
*Assistant Examiner* — Jonathon Cook
(74) *Attorney, Agent, or Firm* — Van Pelt, Yi & James LLP

(57) ABSTRACT

A system for wide-range spectral measurement includes one or more broadband sources, an adjustable Fabry-Perot etalon, and a detector. The one or more broadband sources is to illuminate a sample, wherein the one or more broadband sources have a short broadband source coherence length. The adjustable Fabry-Perot etalon is to optically process the reflected light to extract spectral information with fine spectral resolution. The detector is to detect reflected light from the sample, wherein the reflected light is comprised of multiple narrow-band subsets of the illumination light having long coherence lengths and is optically processed using a plurality of settings for the adjustable Fabry-Perot etalon, and wherein the plurality of settings includes a separation of the Fabry-Perot etalon plates that is greater than the broadband source coherence length but that is less than the long coherence lengths.

16 Claims, 14 Drawing Sheets

FABRY-PEROT SPECTRAL IMAGE MEASUREMENT

CROSS REFERENCE TO OTHER APPLICATIONS

This application claims priority to U.S. Provisional Patent Application No. 62/074,455 entitled MONOLITHIC TUNABLE IMAGING FABRY-PEROT INTERFEROMETER filed Nov. 3, 2014 which is incorporated herein by reference for all purposes.

BACKGROUND OF THE INVENTION

A producer or reseller of items (including ingredients and components of such items)—for example a manufacturer, but also including other parties in the entire supply and distribution chain such as a supplier, a wholesaler, a distributor, a repackager, and a retailer—especially, but not limited to, high-value items, faces counterfeiting of the item. Counterfeiting includes the substitution, dilution, addition or omission of ingredients or components of the item compared to its intended product specification, as well as misrepresentation or diversion of the packaged item from its intended course of sale. This leads to loss of potential revenue as counterfeit items are sold in the place of the real item. Also, there can be health or product related damages caused by not using an authentic item as opposed to a counterfeit—for example, the counterfeit can perform differently or not at all as compared to an authentic item. This is particularly acute in industries that can affect health and safety such as industries involved with pharmaceuticals, nutritional supplements, medical devices, food and beverages, construction, transportation, and defense.

As international criminal organizations become more sophisticated, existing packaging security is proving inadequate. The complexity of many industry supply chains—for example, the supply chain of the pharmaceutical industry—lends itself to entry points for adulterated or counterfeit product(s), often found in carefully counterfeited and high-quality packaging, and sometimes in authentic packaging that has either been stolen or as part of a repackaging operation.

In complex product supply chains and markets with variable pricing, opportunities for arbitrage exist for unscrupulous parties to misrepresent product pricing without any change to the underlying product, and thus benefit monetarily, for example, as in returns, rebate or charge-back fraud. Monetary gain or loss to either side of a transaction may also result from errors in record-keeping.

In addition to counterfeiting or product misrepresentation, items that appear physically identical or similar, for example certain nutritional supplements, may actually contain different ingredients or components, but because of similar appearance may be unintentionally packaged or labeled incorrectly. Even if the items are otherwise identical, they may have different properties associated with the particular lot or batch conditions; for example, pharmaceuticals that otherwise appear identical may have different expiration dates and be incorrectly labeled due to failures or limitations in quality assurance protocols to ascertain such differences.

For product development and research, it may be beneficial at times to study and authenticate performance of items that appear identical but are made differently to learn whether or how those differences affect an end use. At times, it is important in such studies—for example in clinically masked (or 'blind') studies leading to pharmaceutical development—to be able to confidently identify the underlying item without revealing the true identity to study participants. In the case of pharmaceutical development and clinical trials, item-level identity error may be introduced, for example, at the contract research organization that repackages the various product formulations into masked unit-doses. Much time, cost, and effort goes into statistical sampling and chemical analyses to verify the true identity of the unit-doses that are ultimately administered.

In the effort to attain positive health outcomes in a more cost-effective and timely manner, healthcare providers need to focus on the adherence to health regimens, not just the efficacy of specific drugs. Understanding when, where and how often medicine is prescribed by a doctor, accurately and timely dispensed from a pharmacy, received by a patient, and consumed by the patient is helpful in understanding and verifying the effectiveness of the overall health regimen. Recording and collecting the data for appropriate analysis and study while also being able to confirm the underlying identity of the medicine at each stage is important to the reliability of the information collected.

BRIEF DESCRIPTION OF THE DRAWINGS

Various embodiments of the invention are disclosed in the following detailed description and the accompanying drawings.

DETAILED DESCRIPTION

Figure 1:
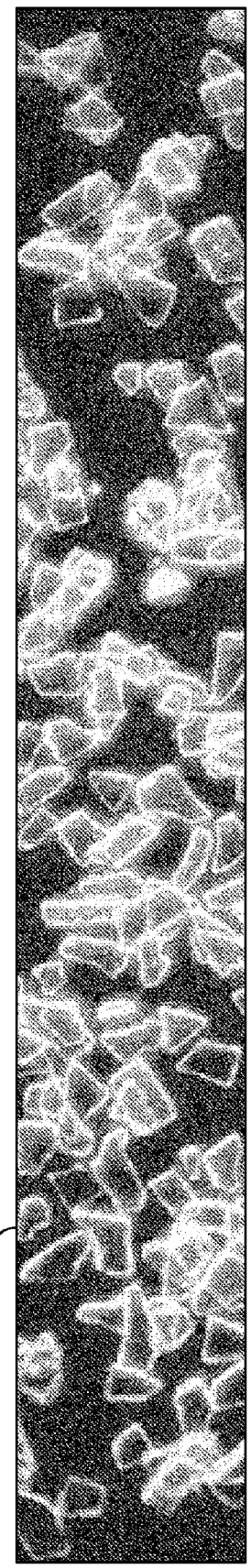
FIG. 1 is an image illustrating an embodiment of a tag.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for wide-range spectral measurement is disclosed The system comprises one or more broadband sources, an adjustable Fabry-Perot etalon, and a detector. The one or more broadband sources are to illuminate a sample, wherein the one or more broadband sources have a short broadband source coherence length. The adjustable Fabry-Perot etalon is to optically process the reflected light to extract spectral information with fine spectral resolution. The detector is to detect reflected light from the sample, wherein the reflected light is comprised of multiple narrowband subsets of the illumination light having long coherence lengths and is optically processed using a plurality of settings for the adjustable Fabry-Perot etalon. The plurality of settings includes a separation of the Fabry-Perot etalon plates that is greater than the broadband source coherence length but that is less than the coherence lengths of the reflected peaks.

In some embodiments, what is unique about the system setup is that one or more wide band sources (this typically means short coherence length) are used but the tag decoding system requires very fine spectral resolution (which in a Fourier-type FPI means the etalon plates need to be scanned to long distances). This is typically self-contradictory (i.e., if coherence is lost over large plate separations, the interference patterns cannot be acquired and the system cannot operate). However, the target tags generate narrow reflection peaks which therefore have long coherence length and so the system as a whole is able to operate.

In some embodiments, the system for relative spectral measurement is specifically configured to measure tags (e.g., rugate tags). In various embodiments, tags comprise one of the following materials: silicon, silicon dioxide, silicon nitride, doped silicon, or any other appropriate material. In some embodiments, tags are made of silica (deemed "generally recognized as safe"—or GRAS—by the FDA), rendering them biologically inert and edible. Each barely visible tag contains a custom-manufactured spectral signature chosen so as to uniquely identify or authenticate a particular product. Tags with a given spectral signature are manufactured in quantities sufficient to enable cost-effective identification of commercial-scale product volumes. The number of available spectral signature combinations range from identifying product manufacturer or brand, to product type or model, to individual lot or batch numbers across multiple industries and markets.

In some embodiments, the unique optical signature of each tag can be read using an absolute or a relative spectral measurement device, apparatus, or system. In some embodiments, tags comprise the surface of a silicon wafer that is etched to have a spectral code encoded by the etching. A thin layer from the surface of the etched wafer is removed and divided into small tags, and the resultant tags contain a complex porous nanostructure that is programmed during electrochemical synthesis to display a unique reflectivity spectrum. The tags are then oxidized by a high-temperature bake step to turn the crystalline, nanoporous silicon tags into amorphous, nanoporous silica. This bake step stabilizes the nanoporous structure against further oxidation (thus stabilizing the spectral signature) and provides for the tags to be characterized as a GRAS excipient.

In some embodiments, the spectrum of one or more tags is measured in an absolute or relative spectral measurement system, then verified against other information as part of a database or located on a label or package. In some embodiments, the tags are used on their own acting simply as labels for quality assurance or other purposes. Information capacity is based on the number of possible unique spectra, using different peak numbers, peak placements, peak rugate phases, and/or peak amplitudes as modulation parameters. The tags are passive, inconspicuous and can be attached to the outside of medicines or food products to be read, for example, through clear or translucent plastic blister packs, or mixed into medicines or food as a forensic excipient, to be read as part of an investigation or inspection process by authorized security or quality assurance personnel.

In various embodiments, the tag properties comprise one or more of the following:
Inconspicuous size range (≈50 to 100 micrometers) allows covert or semi-covert use
Edible and biologically inert
High temperature resistance—melting point above 1000° C.
Passive—no energy input or output
Are used in or on a product, package, label, or security fiber
Are applied via sprays, coatings, varnishes, or as part of laminate
Are integrated at a number of manufacturing stages
High level of security possible; can be scaled to suit specific product needs
Are made so as to be self-authenticating and thereby have a reduced cost and security risk as compared to systems with online databases and maintenance In some embodiments, the system for relative spectral measurement includes a lens for collecting light from the sample with a good working distance and field of view (e.g., ~10 mm diameter field of view, 2× objective lens with numeric aperture (NA) of ~0.05-0.07, and working distance of ~3-7 mm). In some embodiments, the objective lens will be operated in a telecentric arrangement to ensure that the system captures tilted tags.

In some embodiments, lenses in the system for spectral measurement are present to separate the NA of the Fabry-Perot etalon from the NA of the rest of the system. The system has a low NA at the Fabry-Perot etalon to avoid smearing the interferogram because light has traveled through the device at many different angles. In some embodiments, all the lenses are broadband—there is no need for filtering the light with the exception of the Fabry-Perot etalon. In some embodiments the light reaching the detector is bandpass filtered: either by sequentially illuminating with band limited sources, or by placing a series of bandpass filters between the source and the tagged object, or by placing a set of filters in the reflected path between the object and the detector or by utilizing a set of filters on the detector itself, or using a combination of the above. In various embodiments, the Fabry-Perot etalon is made of aluminum coated fused silica, glass or another dielectric, or any other appropriate material. In some embodiments, the outer surfaces of the Fabry-Perot etalon are anti-reflection coated. Scan range of the Fabry-Perot etalon may be tuned from a smallest achievable gap before the plates stick together (e.g., ~500 nm or less) to a gap at which a coherent signal is no longer present (e.g., ~40 um). Depending on the Fabry-Perot etalon finesse, signal processing for the system varies:

a. low finesse Fabry-Perot etalon—after background compensation and optionally tag detection, take a windowed Fourier transform of the interferogram to obtain a tag spectrum.

b. medium finesse Fabry-Perot etalon—after background compensation and potentially tag detection, take a Fourier transform; although the spectrum contains features, deal with the presence of the features rather than try to deconvolve them.

c. high finesse Fabry-Perot etalon—after background compensation and potentially localization of tag position, record the images of transmitted light, determine the relative contribution of interference orders by deconvolving with known RGB color filter response as is known in the art, and continue until all wavelength bands are covered.

d. Use a priori knowledge of the reflected tag spectra in order to detect the spectral signature at ultra-low signal-to-noise regimes.

In some embodiments, because of the telecentric position of the Fabry-Perot etalon, each spot on the sample is imaged to a single spot on the Fabry-Perot etalon. The Fabry-Perot etalon is not required to maintain the same gap everywhere because only a relative spectrum measurement is required. In some embodiments, absolute parallelism is not required, but some reference is required for the system—for example, a laser, to calibrate. In some embodiments, we may be able to work without a reference (e.g., by applying a known spectral feature in the tag, serving as an anchor), thus simplifying and cost-reducing the system. Each object/tag in the image can be processed independently, without the need for normalizing for differences in plate separation. This is different from most imaging interferometer applications, and allows relaxed specifications on optical flatness and coating uniformity, and even coplanarity of the Fabry-Perot etalon.

Figure 2:
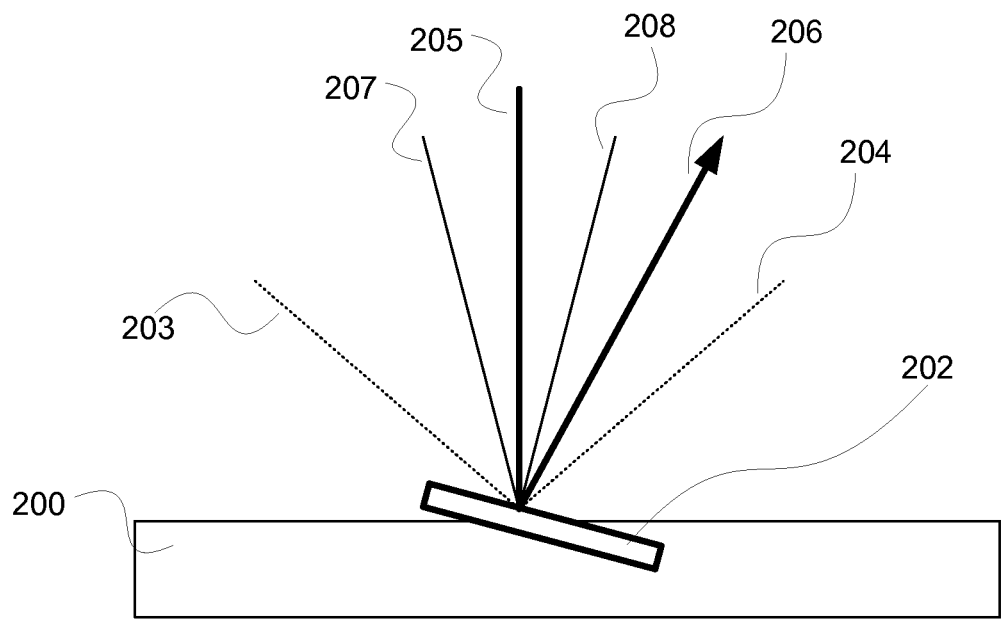
FIG. 2 is a diagram illustrating an embodiment of tag measurement geometry.

FIG. 1 is an image illustrating an embodiment of a tag. In the example shown, tag 100 is a 50 um to 100 um sized irregularly shaped tag. The tags are 20 um thick. These tags are imaged using an Ocean Optics USB2000+ spectrometer with broadband illumination from a halogen source FIG. 2 is a diagram illustrating an embodiment of tag measurement geometry. In the example shown, tag 202 is partially embedded in substrate 200 (e.g., at an angle to the surface of the substrate). Illumination beam (e.g., beam 205) is incident within angular cone outlined by 207 and 208. Collection aperture is different from illumination beam and is outlined with 203 and 204. In this case, the larger collection aperture as compared to the illumination beam enables the collection of reflected light from tilted tags. In some embodiments, beam 206 is reflected beam from incident beam 205.

Figure 3:
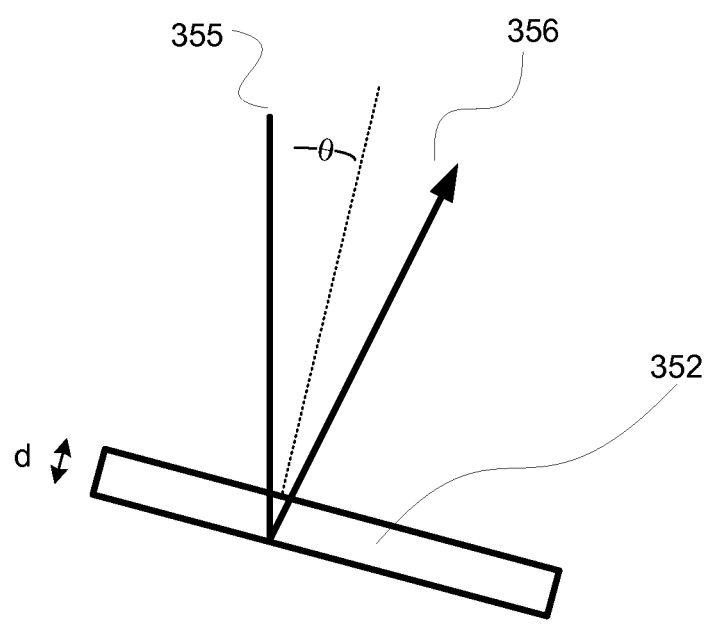
FIG. 3 is a diagram illustrating an embodiment of spectral dependence associated with geometry.

FIG. 3 is a diagram illustrating an embodiment of spectral dependence associated with geometry. In the example shown, tag 352 surface normal is angle θ with respect to incident light 355. A reflected spectral peak location is a function of the optical path length of the beam within the tag. The path is a function of the angle between the light ray and the surface of the tag and is proportional to d/cos(θ). Thus, the spectrum from a tilted tag is shifted. In addition, the peaks broaden and become lower (perhaps due to scattering within the tag). In some embodiments, beam 356 is reflected beam from incident beam 355.

In some embodiments, the reflections of multiple tags at different angles will broaden the reflection peaks. In some embodiments, variations in tags also will broaden the reflection peaks.

Figure 4:
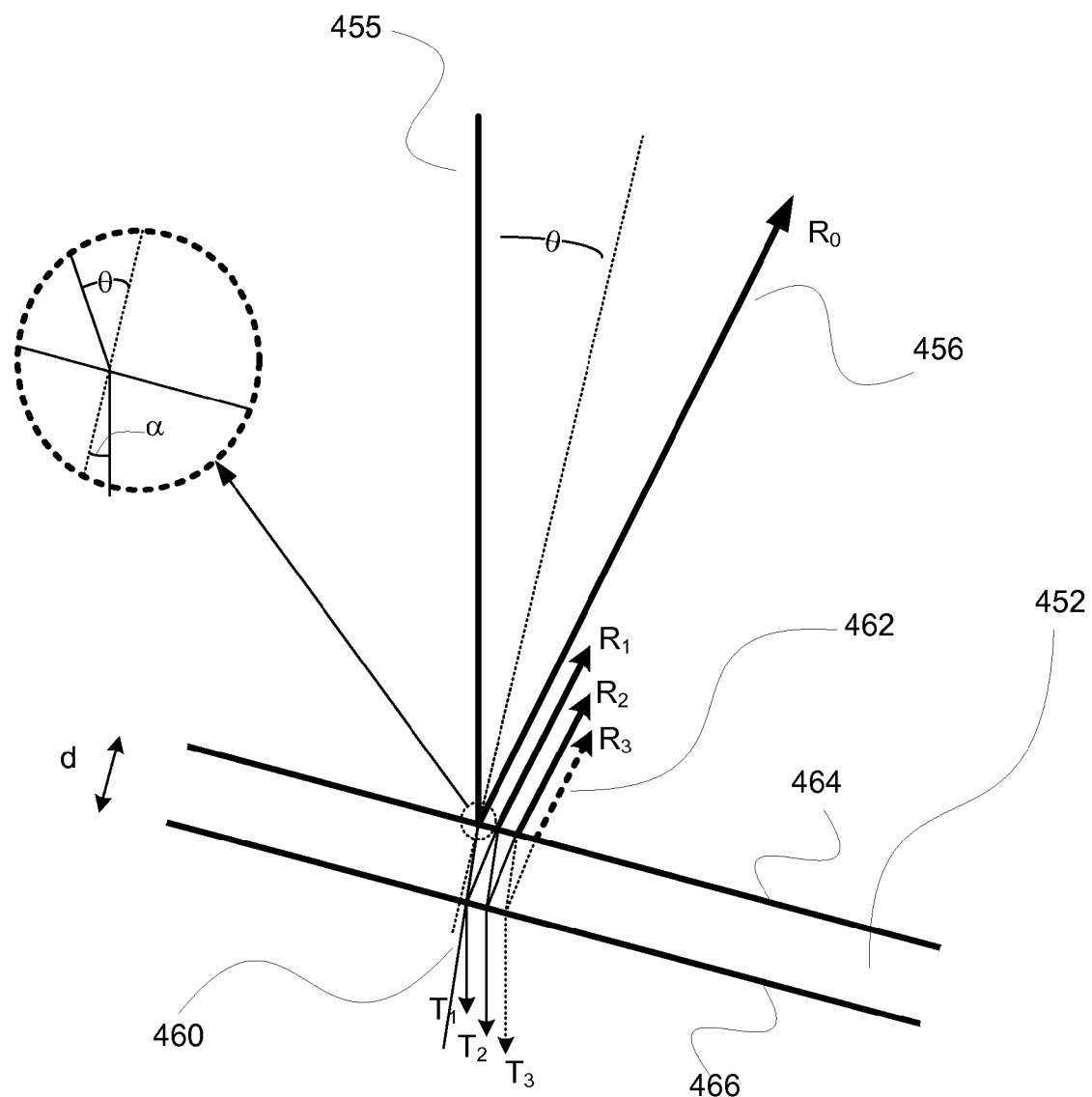
FIG. 4 is a diagram illustrating an embodiment of a Fabry-Perot etalon.

In some embodiments, the tags are specular reflectors and not diffuse reflectors. Therefore, the tags can either be illuminated at a large angle orthogonal to the object surface, or the tags can be combined using a diffuser and lens to form a combined multispectral high NA beam orthogonal to the surface FIG. 4 is a diagram illustrating an embodiment of a Fabry-Perot etalon. A related device is the Fabry-Perot Interferometer or etalon. The heart of the Fabry-Perot etalon (e.g., etalon 452) is a pair of partially reflective surfaces (e.g., surface 464 and surface 466) spaced hundreds of nanometers to centimeters apart (e.g., d). Light is incident at an angle θ to the normal of surface 464. The first reflection 456 is $R_0$. Within etalon 452 light travels at angle α to the normal of surface 466 (see also close up). The varying transmission function of the etalon is caused by interference of the multiple reflections of light between the two reflecting surfaces. Producing beams transmitted 460 ($T_1$, $T_2$, $T_3$, etc.) and reflected 462 ($R_1$, $R_2$, $R_3$, etc.). Constructive interference occurs if the transmitted beams are in phase, and this corresponds to a high-transmission peak of the etalon. If the transmitted beams are out-of-phase, destructive interference occurs and this corresponds to a transmission minimum. Whether the multiple reflected beams are in phase or not depends on the wavelength (λ) of the light, the angle the light travels through the etalon (α), and the local thickness of the etalon (d). In the equations below, the plates are separated by a space with a refractive index n (e.g., for air n=1) and the propagation of light into the plates is negligible or independent of wavelength. The phase difference between each successive transmitted pair (e.g., $T_2 - T_1$) is given by δ:

$$\delta = (2\pi/\lambda) 2nd \cos \alpha$$

If both surfaces have a reflectance R, the transmittance function of the etalon is given by:

$$T_e = \frac{(1-R)^2}{1 + R^2 - 2R\cos\delta} = \frac{1}{1 + F\sin^2(\delta/2)},$$

where the coefficient of finesse (F) is $$F = \frac{4R}{(1-R)^2}$$

Figure 5A:
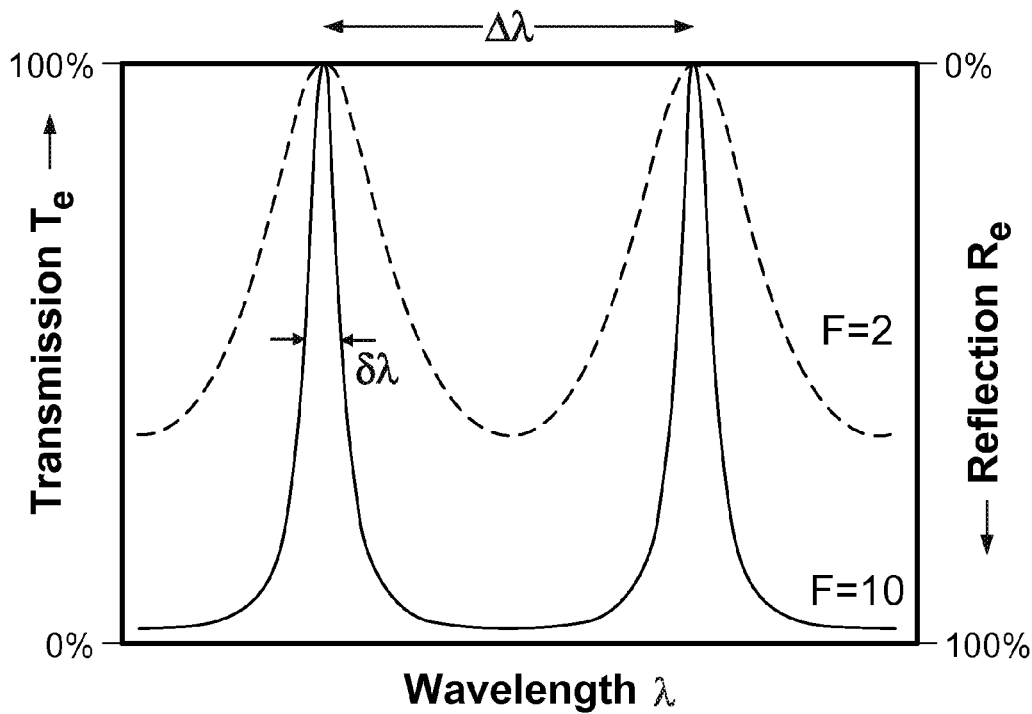
FIG. 5A is a graph illustrating an embodiment of the transmission of an etalon.

FIG. 5A is a graph illustrating an embodiment of the transmission of an etalon. In the example shown, maximum transmission of the etalon ($T_e=1$) occurs when the optical path length difference, $2nd \cos \alpha$, between each transmitted beam is an integer multiple of the wavelength ($\lambda$). In the absence of absorption, the reflectance of the etalon $R_e$ is the complement of the transmittance, such that $T_e+R_e=1$. The maximum reflectivity is given by:

$$R_{max} = 1 - \frac{1}{1+F} = \frac{4R}{(1+R)^2}$$

and this occurs when the path-length difference is equal to half an odd multiple of the wavelength. A high-finesse etalon (F=10) shows sharper peaks and lower transmission minima than a low-finesse etalon (F=2). The wavelength separation between adjacent transmission peaks is called the free spectral range (FSR) of the etalon, $\Delta\lambda$, and is given by:

$$\Delta\lambda = \lambda^2_0/2nd \cos \alpha + \lambda_0)$$

where $\lambda_0$ is the central wavelength of the nearest transmission peak. The FSR is related to the full-width half-maximum, $\delta\lambda$, of any one transmission band by a quantity known as the finesse:

$$\mathcal{F} = \frac{\Delta\lambda}{\delta\lambda} = \frac{\pi}{2\arcsin(1/\sqrt{F})}$$

A Fabry-Perot etalon is able to adjust the distance d between the reflective surfaces in order to change the wavelengths at which transmission peaks occur in the etalon. Due to the angular dependence of the transmission, the peaks can also be shifted by rotating the etalon with respect to the beam or if the beam enters the etalon at an angle. In this case, the transmitted wavelengths will shift by the cosine of its angle with the plates. This result is important because it means that if light is not perfectly collimated as it enters the etalon, the transmission peaks will be broadened and spectral resolution will be decreased. This angular dependence has different effects depending on the optical configuration in which the etalon is used. In a telecentric case, at each location on the entrance plane to the etalon, rays are entering at a different angle. Therefore, the spectral response at each location will be different, although the effect of plate flatness or non-coplanarity will be reduced. For a given plate separation, multiple wavelengths will be transmitted through the device. For a given Finesse, as the wavelength resolution increases, the FSR decreases.

Figure 5B:
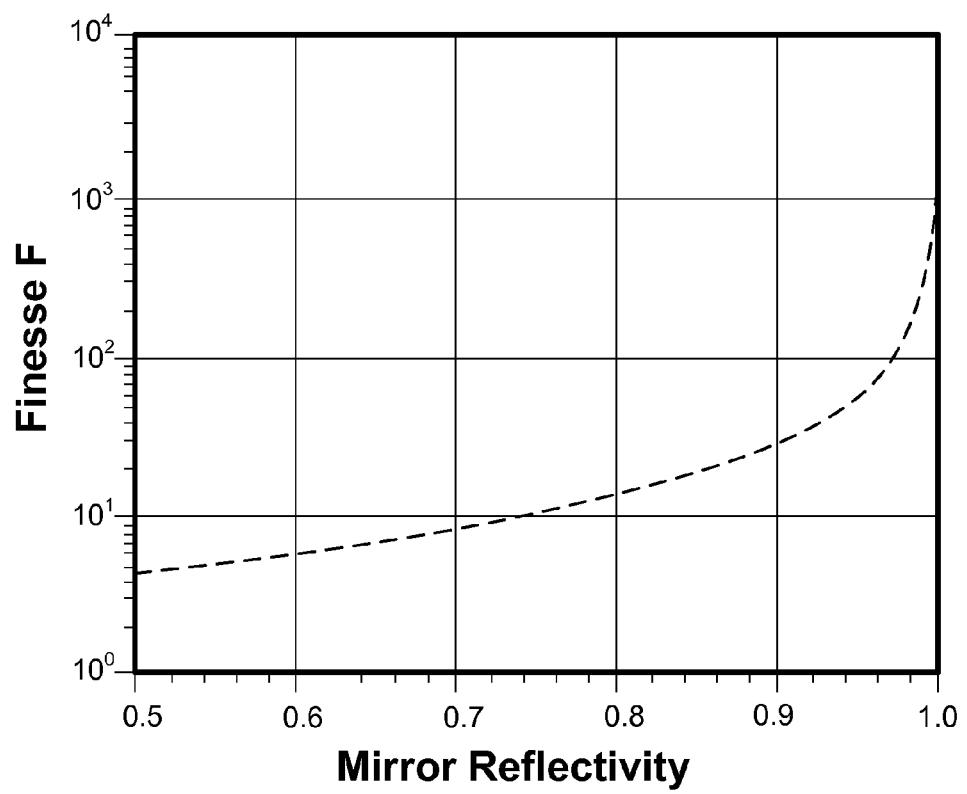
FIG. 5B is a graph illustrating an embodiment of the finesse as a function of the reflectivity of the surfaces of the etalon.

FIG. 5B is a graph illustrating an embodiment of the finesse as a function of the reflectivity of the surfaces of the etalon. In the example shown, high finesse factors correspond to high reflectivity of the etalon surfaces.

Figure 6:
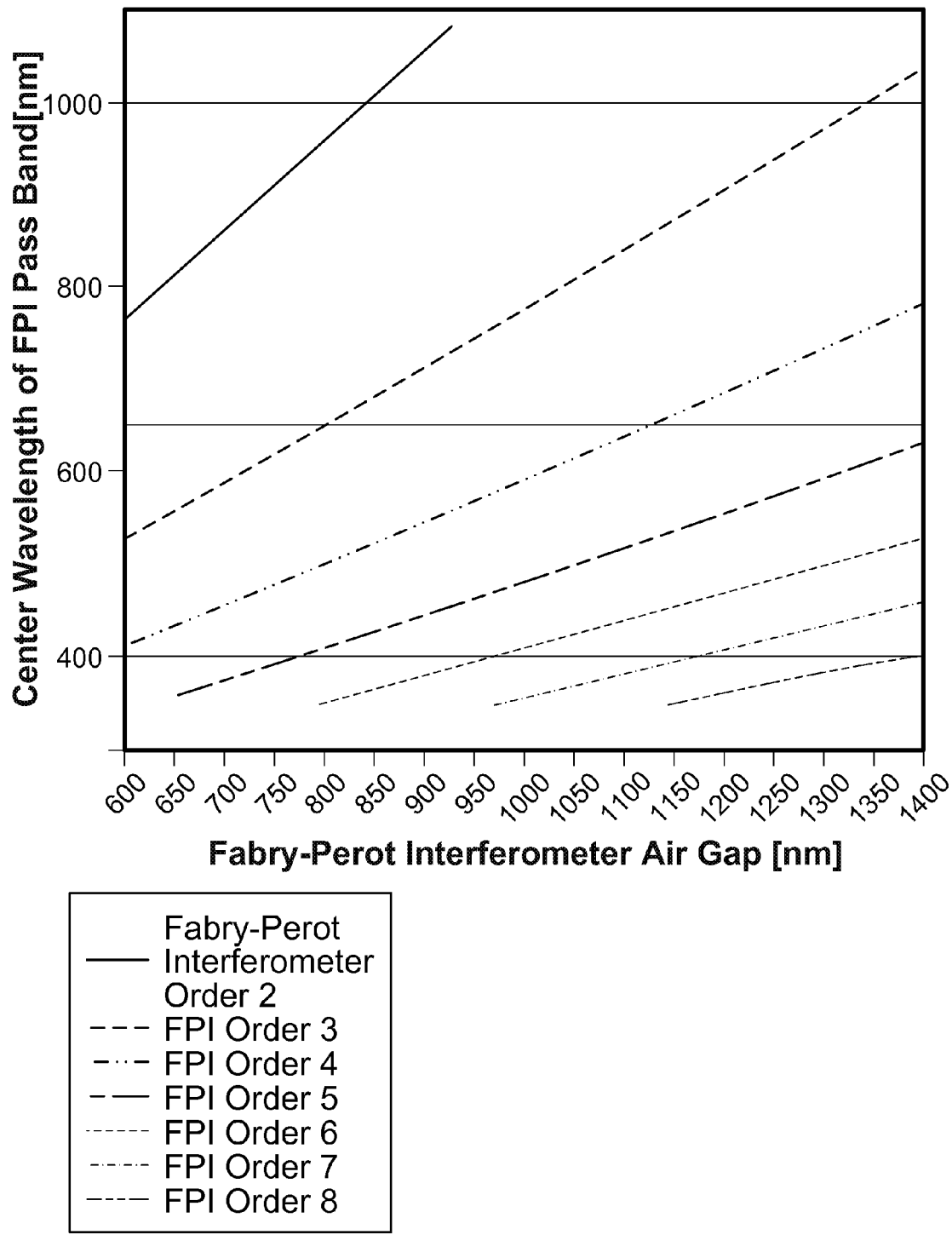
FIG. 6 is a graph illustrating an embodiment of center wavelength transmitted through a Fabry-Perot etalon for different gaps between the surfaces.

FIG. 6 is a graph illustrating an embodiment of center wavelength transmitted through a Fabry-Perot etalon for different gaps between the surfaces. For a given plate separation, multiple wavelengths will be transmitted through the device. In some embodiments inserting a bandpass filter ensures that wavelengths from only one interference pattern enter the Fabry-Perot etalon. By using different bandpass filters, different orders through the Fabry-Perot etalon can be identified. For example, using a multispectral image sensor at the exit of the Fabry-Perot etalon, such that by looking at the relative amplitude of light on different pixels, one can deduce which harmonics was transmitted through the Fabry-Perot etalon. In some embodiments, two Fabry-Perot etalons are used in series to isolate one order—the first having a low finesse and acting as a bandpass filter to select a limited band of light, narrower than the FSR of the second Fabry-Perot etalon, which has a high Finesse (low FWHM with narrow FSR). Note that implementations where the device is used as a bandpass filter are very lossy in terms of their energy utilization, because only a tiny fraction of the incoming light is transmitted through the device and is used for generating the spectrum.

For a typical Fourier-Transform Fabry-Perot Interferometer (FT FPI), the two parallel partially-reflective mirrors of the Fabry-Perot etalon are utilized in a different way. FT-FPI's take 2D images of the (in the ideal case) monochromatic light exiting the Fabry-Perot etalon for each inter-plate separation, to generate a hyperspectral cube. In other words, an inter-plate separation is set (d), and a two-dimensional image of an illuminated object is taken that gives frequency information of the light reflected from the object. To obtain an accurate representation of the entirety of the spectrum a zero separation (e.g., d=0) image must be included in the interferogram. However this is not practical given both photon penetration depth into the glass coating material and the tendency of 2 flat plates to adhere if placed in close proximity. Multiple methods have been developed in order to get around this problem, including inferring the small gap portion of the interferogram from the Fourier transform of the accessible portion of the interferogram along with a priori knowledge of the spectrum to be measured. For producing a device with a narrowly defined function such as measuring tags, more a priori knowledge is available and tis is less of a problem.

Also, ideally for the FT-FPI the light incident has long coherence length for all the wavelengths that are desired to be measured. The operation of the FT-FPI is based on the coherence of the reflected light. In other words, as wave fronts pass through multiple reflections, they must remain in-phase in order for them to consistently interfere. This is less an issue for laser light which is highly coherent, but when a broadband or white light source (e.g., from an LED) passes multiple times through plates which are placed far apart, this can impose a critical constraint on the system. For example, assume a maximum separation of 1 mm between the plates and a reflectivity such that the amplitude of reflected light is still significant after 10 reflections, this translates to a total coherence length requirement of 10 mm. But a typical coherence length of a broadband or white light source is a few hundred nanometers to a few microns. This can limit the number of interference orders which are used in the transform and therefore the quality of the resultant spectrum that is measured by the FT-FPI.

The characteristics of the tags being measured enable a specialized variant of a Fourier-Transform Fabry-Perot Interferometer. The system for relative spectral measurement differs from FT-FPI as follows:

No bandpass filter needed at entrance (e.g., no bandpass filter between the sample and the Fabry-Perot etalon). The spectral location of the tag (e.g., rugate peaks) assures sufficiently low spectral content in longer wavelengths. Thus, no bandgap or low-pass filter is required at the entry to prevent ambiguity in the resultant spectrum.

Large distance d range can be scanned with incoherent wide band source (e.g. 400-900 nm). The tag-generated peaks are quite narrow (5 nm-20 nm). Since coherence length increases as the inverse of linewidth, the tag reflectance characteristics in effect extend the usable range of the FT-FPI. For example, at 850 nm, a conservative estimate of the coherence length of the rugate peaks is 36 µm with a 20 nm (widest possible) peak FWHM. Therefore, the device can be operated with long separation ranges to yield good Fourier Transform results. In contrast, if the peak was not present and we were trying to image an object with a 200 nm spectral content, the coherence length would have been only 3.6 µm and we would not be able to generate a reliable Fourier Transform. A typical FT-FPI would not be able to function properly across the required spectral range unless objects such as the tags significantly reduce the linewidth of the observed object.

The manufacturing tolerances can be greatly relaxed (e.g., tens of nanometers). Specifically, because the spectral response is a function of the separation between the surfaces, non-flatness or roughness of either surface results in spectral broadening (e.g., localized averaging of the phases) as well as a spectral response which is a function of position on the device—each point in the image cannot be interpreted as corresponding to the same wavelength (or in the case of curved surface of an FT-FPI a smoothly varying wavelength). However, because only relative spectral measurements are being measured, each image point can be interpreted separately not absolutely and therefore calibrated individually. As an example, for the relative measurement system each element samples a unique area element of the object, on the order of or smaller than a single tag (e.g., a 100 mm$^2$ region is imaged using a 10 MPixel sensor, then a 100 µm diameter tag will span $0.1^2/10^2 \times 10^7 = 1,000$ pixel). Each such area element will have a slightly different spectral response, but the FWHM will still be narrow, especially if plate reflectivity is kept low such that each beam makes only one round trip before it is significantly attenuated.

No requirement for zero separation of plates. The tag signal can be decoded without knowing absolute wavelength: As discussed above, prior work on FT-FPI required OPD to be scanned from zero separation to a sufficiently large separation (such that many interference orders are recorded) in order to perform a Fourier Transform. This imposes difficult constraints on the design of the plates, to prevent them from sticking together. We perform a Finite Fourier Transform starting from a finite separation and miss some lower interference orders. Thus, strictly speaking, the system comprises not a Fourier-Transform Fabry-Perot interferometer but rather a Finite-Fourier-Transform Fabry-Perot interferometer, and delivers not an absolute spectrum but rather a relative spectrum which varies by position across the detector array. While unacceptable from most hyperspectral imaging applications, this is absolutely acceptable for decoding tags and enables a lower complexity and lower cost device.

Figure 7:
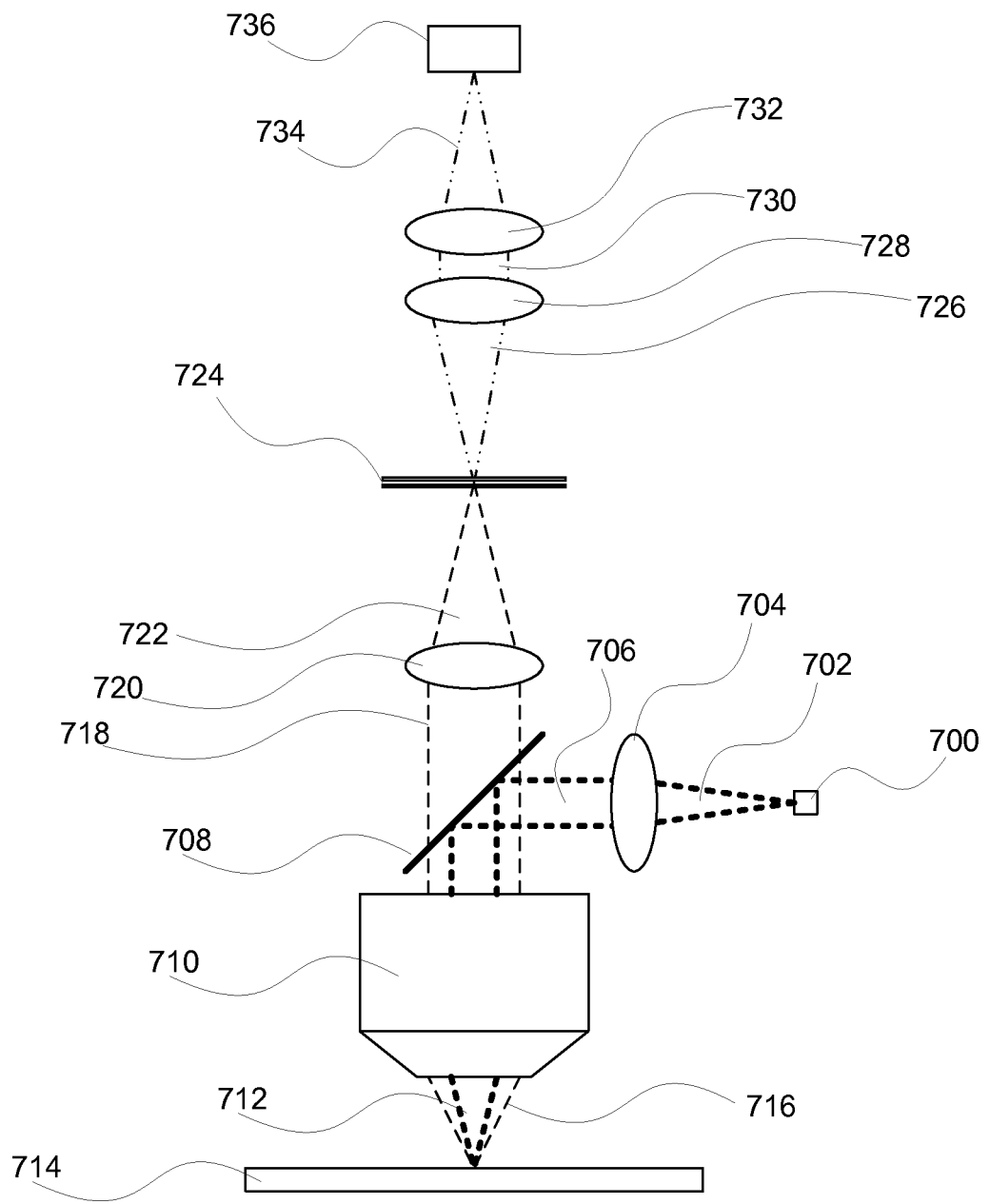
FIG. 7 is a diagram illustrating an embodiment of a system for relative spectral measurement.

FIG. 7 is a diagram illustrating an embodiment of a system for relative spectral measurement. In the example shown, source 700 provides broadband illumination to sample sitting on or in substrate 714. For example, source 700 comprises a white light emitting diode, a tungsten source, an incandescent source, or any other appropriate source. Light from source 700 propagates along path 702 and is collimated using lens 704. Light propagates along path 706 and at least a portion is reflected by beam splitter 708 through objective 710, travels on path 712, and is focused on sample on substrate 714. Reflected light from sample on sample substrate 714 propagates along path 716. Numerical aperture of incident beam is different from the numerical aperture of the reflected beam (e.g., NA of incident beam is smaller than NA of reflected beam).

In the example shown, reflected light from sample is collimated and propagates along 718 with at least a portion of the beam transmitting through beam splitter 708. The reflected light is focused using lens 720 to focus on Fabry-Perot etalon 724 on path 722. For example, the reflected light of the sample is imaged on to the Fabry-Perot etalon (e.g., Fabry-Perot etalon 724). The transmitted light through Fabry-Perot etalon 724 propagates along path 726 to lens 728 and lens 732 so that the transmitted light propagates along path 730 and path 734. Transmitted light is focused on detector 736. For example, the filtered reflected light from the sample is imaged onto the detector (e.g., detector 736). Detector 736, Fabry-Perot etalon 724, and sample on sample substrate 714 are each optically at the same point (e.g., telecentric). In some embodiments, detector 736 and Fabry-Perot etalon 724 are separated by imaging optics (e.g., one or more lenses).

Figure 8:
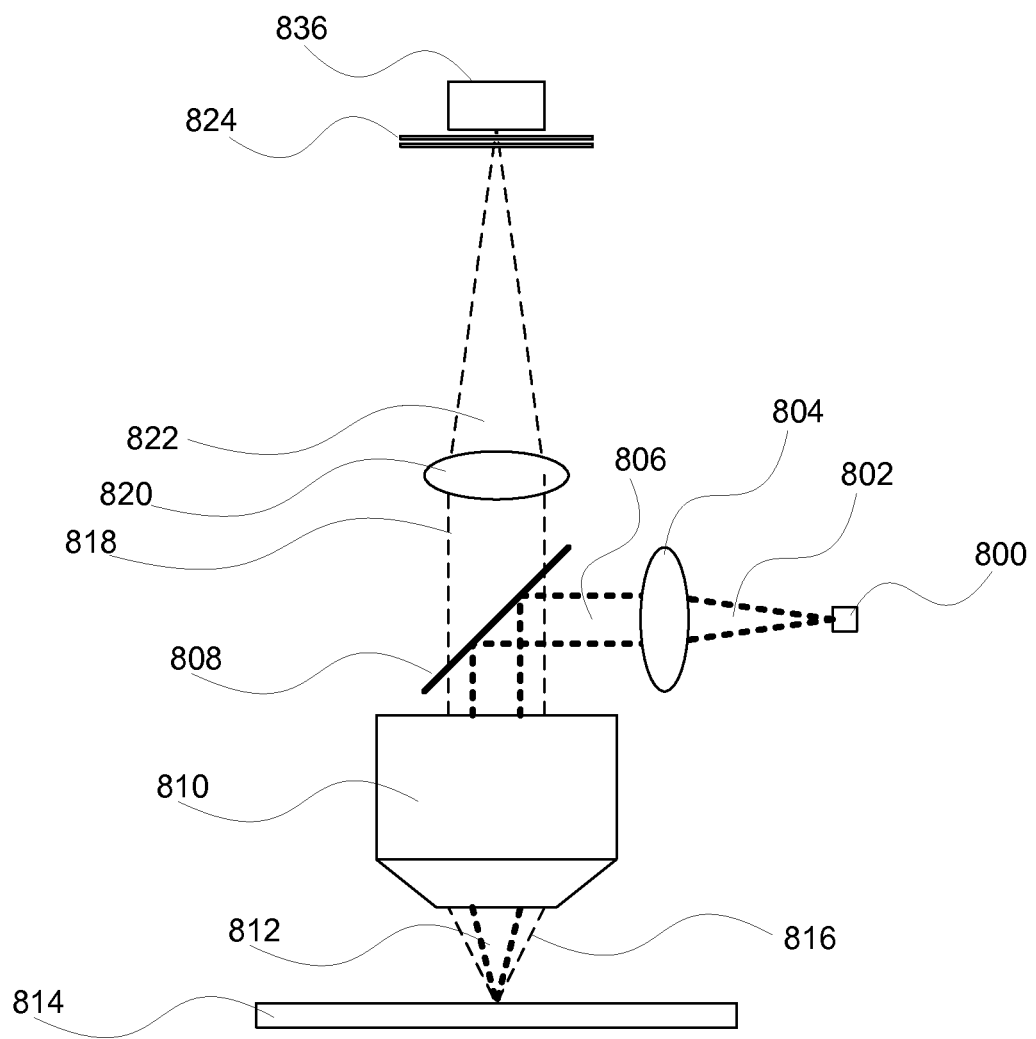
FIG. 8 is a diagram illustrating an embodiment of a system for relative spectral measurement.

FIG. 8 is a diagram illustrating an embodiment of a system for relative spectral measurement. In the example shown, source 800 provides broadband illumination to sample sitting on or in substrate 814. For example, source 800 comprises a white light emitting diode, a tungsten source, an incandescent source, or any other appropriate source. Light from source 800 propagates along path 802 and is collimated using lens 804. Light propagates along path 806 and at least a portion is reflected by beam splitter 808 through objective 810, travels on path 812, and is focused on sample on substrate 814. Reflected light from sample on sample substrate 814 propagates along path 816. Numerical aperture of incident beam is different from the numerical aperture of the reflected beam (e.g., NA of incident beam is smaller than NA of reflected beam).

In the example shown, reflected light from sample is collimated and propagates along 818 with at least a portion of the beam transmitting through beam splitter 808. The reflected light is focused using lens 820 to focus on Fabry-Perot etalon 824 on path 822. The transmitted light through Fabry-Perot etalon 824 propagates directly to detector 836. Detector 836, Fabry-Perot etalon 824, and sample on sample substrate 814 are each optically close to the same point.

In some embodiments, Fabry-Perot etalon 824 and detector 836 are combined in an integrated device. The integrated device addresses the following problems:

Co-location of the Fabry-Perot cavity with the detector on the focal plane to maximize spatial and spectral performance Reduction of system complexity, robustness, and cost by reducing the number of optical elements.

In some embodiments, the integrated device integrates the image sensor (e.g., a complementary metal-oxide-semiconductor (CMOS) Image Sensor, charge coupled device (CCD), or any other array sensor) as the back-reflector of a Fabry-Perot etalon. Typically, Fabry-Perot etalon surfaces or plates need to have the following performance:

Known and preferably controlled reflectivity (e.g., by applying a specific coating)

Flat, typically less than the shortest wavelength of light to be passed through the FPI.

In some embodiments, the front surface of CMOS Image Sensors (CIS) is not used. Specifically, because the front surface of the CIS contains a stack of metal lines separated by dielectrics with additional structures on top, the top surface typically has local non-planarity in the micron range, and even polishing cannot achieve tens of nanometers peak to valley flatness. Furthermore, for this reason and because of patterning of the top surface, the reflectivity varies across the top surface of the CIS die.

In some embodiments, backside-illuminated (BSI) CIS technologies have the back surface of the CIS wafer that is backgrinded, and photons impinge on the back surface of the die, are absorbed in the silicon and collected and processed as before. In this scheme, the side exposed to the light is flat (e.g., unpatterned and typically polished silicon). This side can be coated by anti-reflective coating to reduce or control its reflectivity. In some embodiments, that surface is polished to reach "optical" quality of tens of nanometers peak to valley across a die. This surface can be used as the back plate of a Fabry-Perot etalon.

In various embodiments, the relative spectral measurement device comprises a fixed and/or a tunable Fabry-Perot etalon, both integrated with the array detector such that it forms a monolithic unit.

Figure 9:
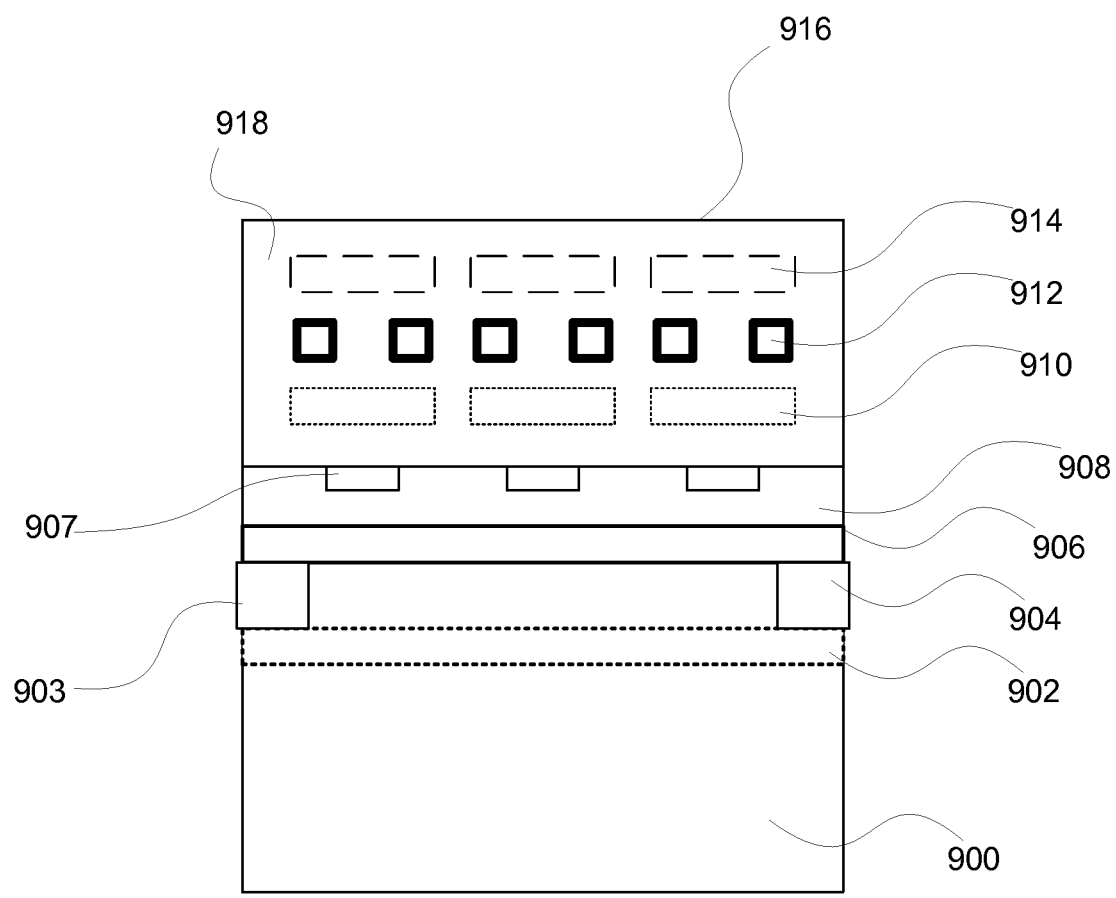
FIG. 9 is a diagram illustrating an embodiment of an integrated device with a Fabry-Perot etalon and an adjacent detector.

FIG. 9 is a diagram illustrating an embodiment of an integrated device with a Fabry-Perot etalon and an adjacent detector. In some embodiments, the integrated device of FIG. 9 is used to implement Fabry-Perot etalon 824 and detector 836 of FIG. 8. In the example shown, glass 900 has thin metal coating 902 separated from anti-reflective coating 906 by spacer 903 and spacer 904. In various embodiments, spacer 903 and spacer 904 comprise a plurality of static spacers, active spacers, Micro-Electro-Mechanical Systems (MEMS) movers or stagers, piezoelectric movers or stages, or any other appropriate spacers between the front reflector and the CMOS detector die. In some embodiments, three stages are attached so that coplanarity is achievable between the two surfaces of the Fabry-Perot etalon by adjusting the stages. Anti-reflective coating 906 is coupled to silicon substrate 908 with photodiodes 907. Silicon substrate 908 with photodiodes 907 is coupled with silicon dioxide inter-metal dielectric 918 with metal wires embedded (e.g., metal wires 910, metal wires 912 and metal wires 914). The top comprises front side 916 of the integrated device. Illumination is from the bottom.

In some embodiments, the back surface of the BSI wafer is polished to achieve desired flatness.

In some embodiments, an etch stop layer is deposited on the back surface of the wafer such that a uniform-thickness layer is formed—for example, using Atomic Layer Deposition.

In some embodiments, the anti-reflective coating on the back side of the silicon die is present. In some embodiments, the anti-reflective coating on the back side of the silicon die is not present. In some embodiments, there is a thin metal coating on the back side of the silicon die and no anti-reflective coating. In the event that no coating is used, the reflectivity of the silicon surface as a function of wavelength must be taken into account when calculating the spectral response of the monolithic device. In some embodiments, the spectral response of the anti-reflective coating is designed—for example, such that it complements the reflectivity of the silicon surface resulting in a spectrally flat response. In some embodiments, a thin metal coating is applied on the silicon surface such that the target reflectivity is reached, while a sufficiently high portion of the light (e.g., 20% reflectivity and 80% transmissivity) is transmitted to the photodiodes in the silicon die.

In some embodiments, an important feature of the glass—BSI CMOS—spacer and the glass—BSI CMOS with a tunable MEMS interposer configurations is that they are amenable to wafer-level integration, and is thus very cost effective.

Figure 10A:
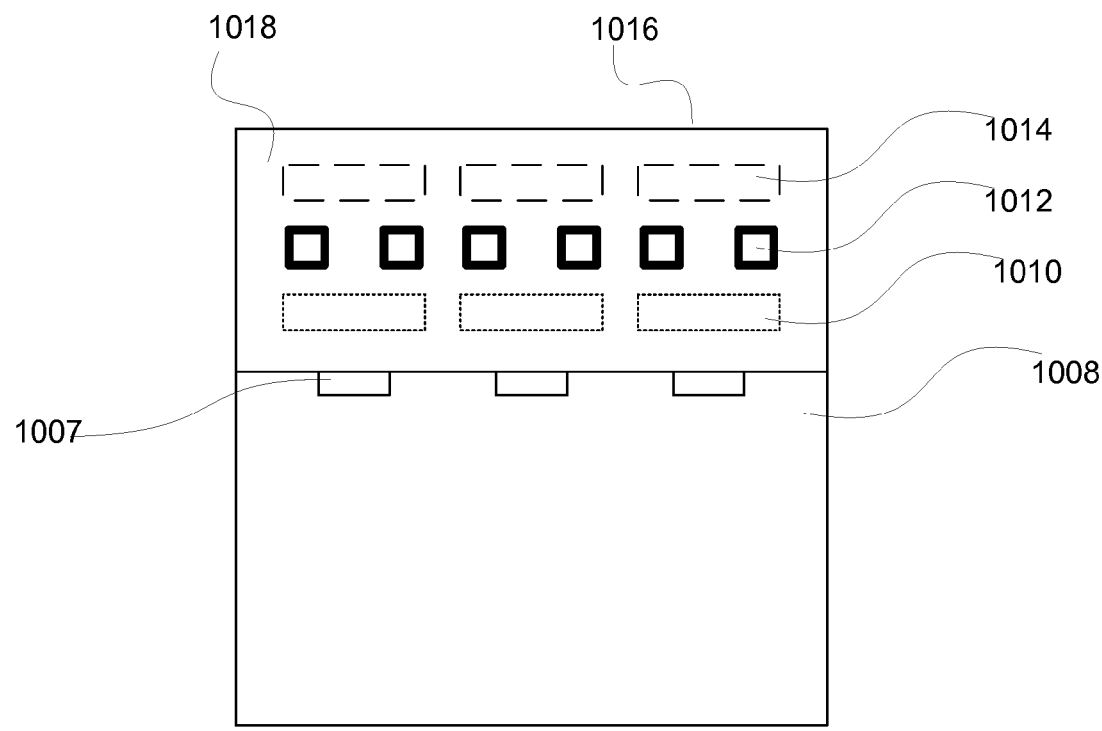
FIG. 10A is a diagram illustrating an embodiment of a step in producing the integrated device.

FIG. 10A is a diagram illustrating an embodiment of a step in producing the integrated device. In the example shown, a CIS wafer is fabricated. Silicon substrate 1008 with photodiodes 1007 is coupled with silicon dioxide inter-metal dielectric 1018 with metal wires embedded (e.g., metal wires 1010, metal wires 1012 and metal wires 1014). The top comprises front side 1016 of the integrated device.

Figure 10B:
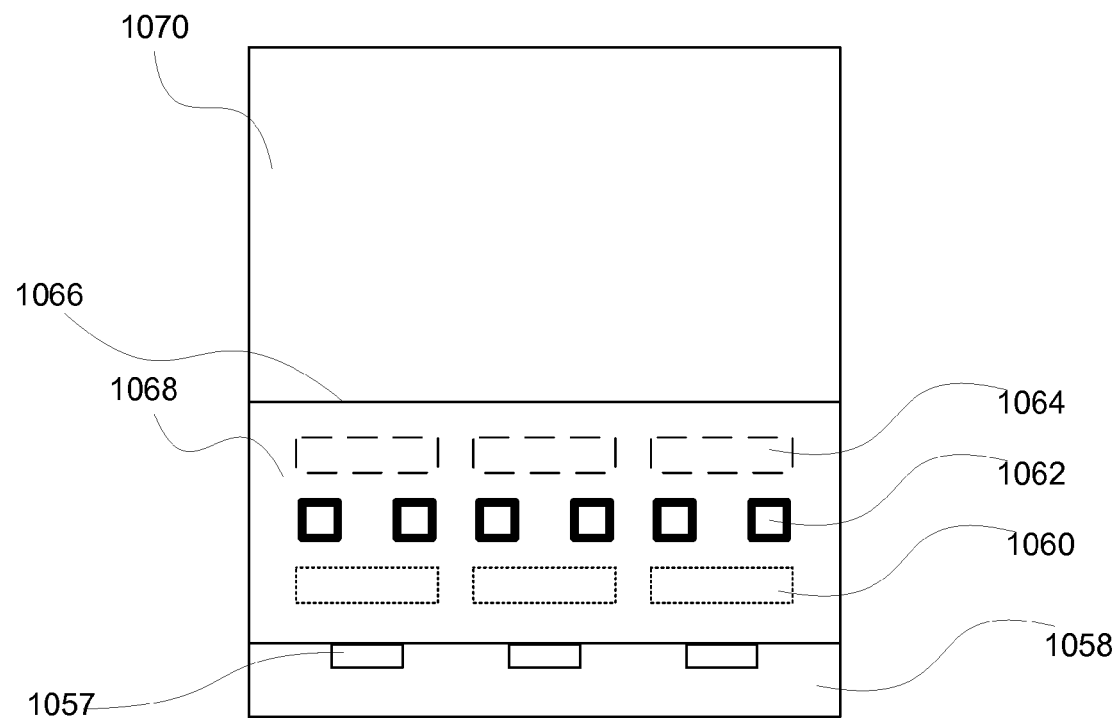
FIG. 10B is a diagram illustrating an embodiment of a step in producing the integrated device.

FIG. 10B is a diagram illustrating an embodiment of a step in producing the integrated device. In the example shown, handle wafer 1070 is attached to front surface 1066, and silicon substrate 1058 is etched to the desired thickness and subsequently polished to the desired flatness. Silicon substrate 1058 with photodiodes 1057 is coupled with silicon dioxide inter-metal dielectric 1068 with metal wires embedded (e.g., metal wires 1060, metal wires 1062 and metal wires 1064). The top comprises front side 1016 of the integrated device.

Figure 11A:
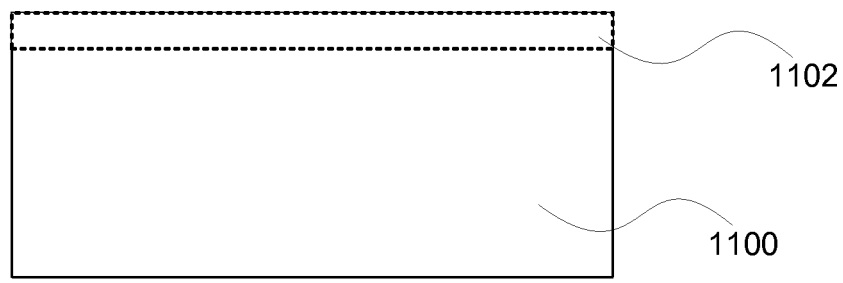
FIG. 11A is a diagram illustrating an embodiment of a step in producing the integrating device.

FIG. 11A is a diagram illustrating an embodiment of a step in producing the integrating device. In the example shown, glass or quartz wafer 1100 (e.g., nominal thickness or previously backgrinded and optionally attached to a handle wafer from the bottom) is coated by a metal film 1102 (e.g., metal coating).

Figure 11B:
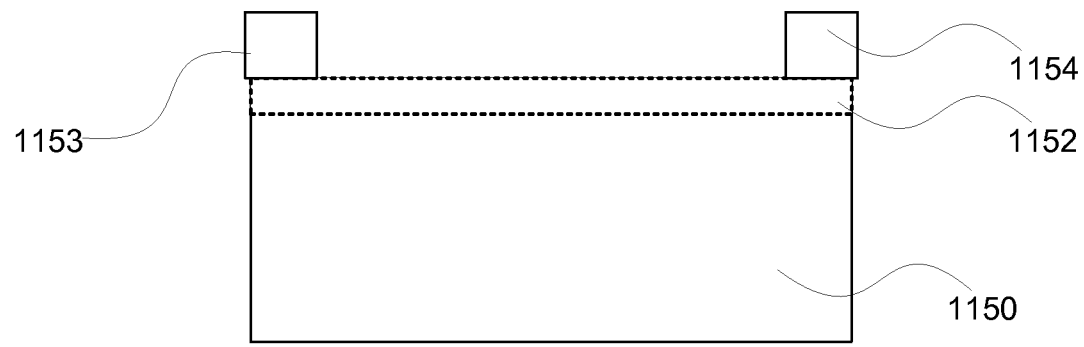
FIG. 11B is a diagram illustrating an embodiment of a step in producing the integrating device.
Figure 12:
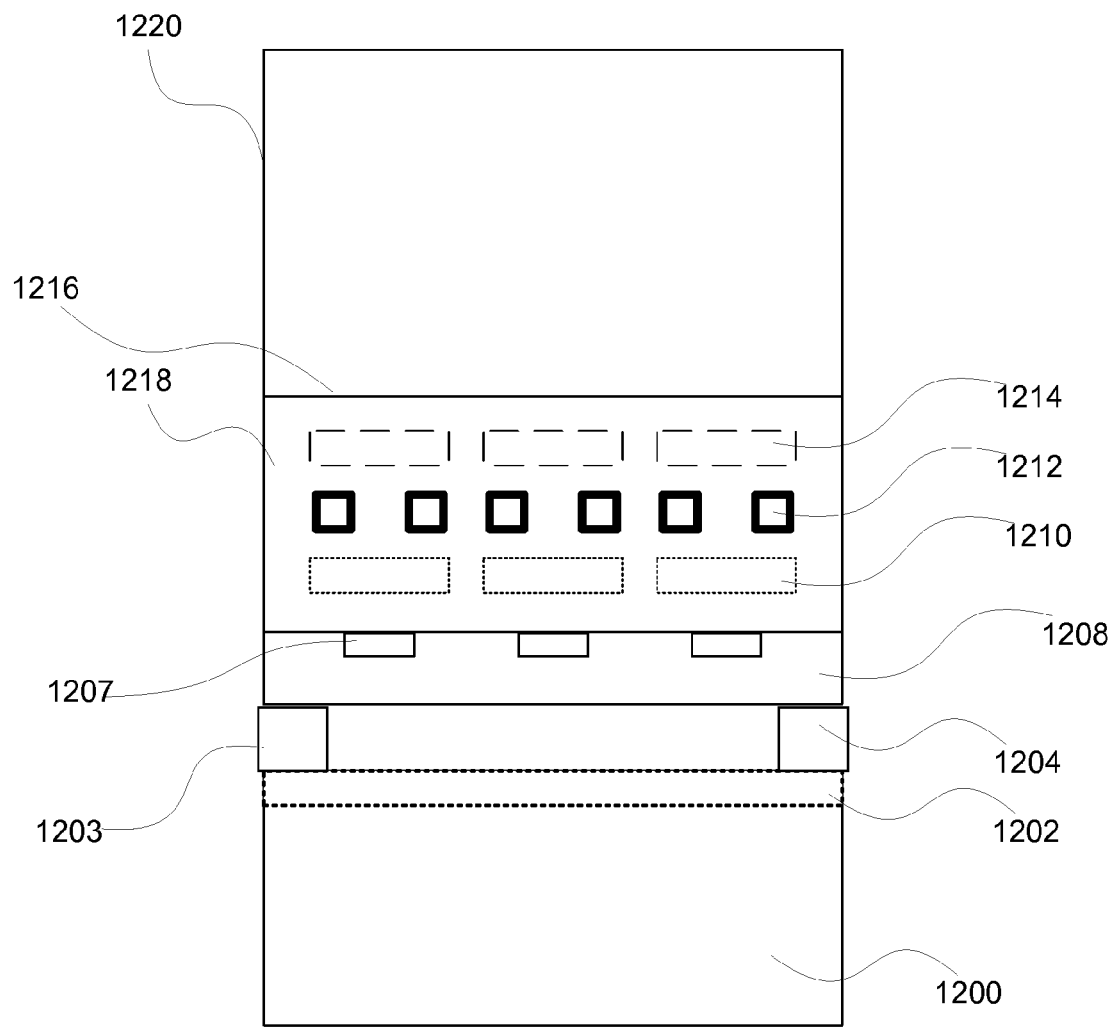
FIG. 12 is a diagram illustrating an embodiment of a step in producing the integrating device.

FIG. 11B is a diagram illustrating an embodiment of a step in producing the integrating device. In the example shown, glass or quartz wafer 1150 (e.g., nominal thickness or previously backgrinded and optionally attached to a handle wafer from the bottom) is coated by a metal film 1152 (e.g., metal coating). A spacer (e.g., spacer 1153 and spacer 1154) is either deposited and patterned (e.g., using polyimide) or is wafer-bonded (e.g., similar to bonding of interposer wafers as is known in the industry), or is etched from the original glass wafer prior to the thin metal film coating. In all cases, the spacer is patterned such that the wafers' separation is similar to the dimension of the dies on the CIS wafer. More specifically, in the case of a polyimide spacer, the process flow is:

Spin coat polyimide and cure
Optionally polish the polyimide
Photolithographically etch the non-spacer regions FIG. 12 is a diagram illustrating an embodiment of a step in producing the integrating device. In the example shown, the glass wafer and CIS wafer are aligned and bonded—for example, by heating the polyimide layer while concurrently co-planarizing the wafers and cooling. Glass 1200 has thin metal coating 1202 separated from silicon substrate 1208 by spacer 1203 and spacer 1204. In various embodiments, spacer 1203 and spacer 1204 comprise static spacers, active spacers, Micro-Electro-Mechanical Systems (MEMS), piezoelectric movers, or any other appropriate spacers. Silicon substrate 1208 includes photodiodes 1207. Silicon substrate 1208 with photodiodes 1207 is coupled with silicon dioxide inter-metal dielectric 1218 with metal wires embedded (e.g., metal wires 1210, metal wires 1212 and metal wires 1214). Handle wafer 1220 is attached to front surface 1216. In some embodiments, the handle wafer is de-bonded.

In some embodiments, the CIS is electrically and mechanically bonded to an electrical substrate as is done with CIS camera modules.

Figure 13:
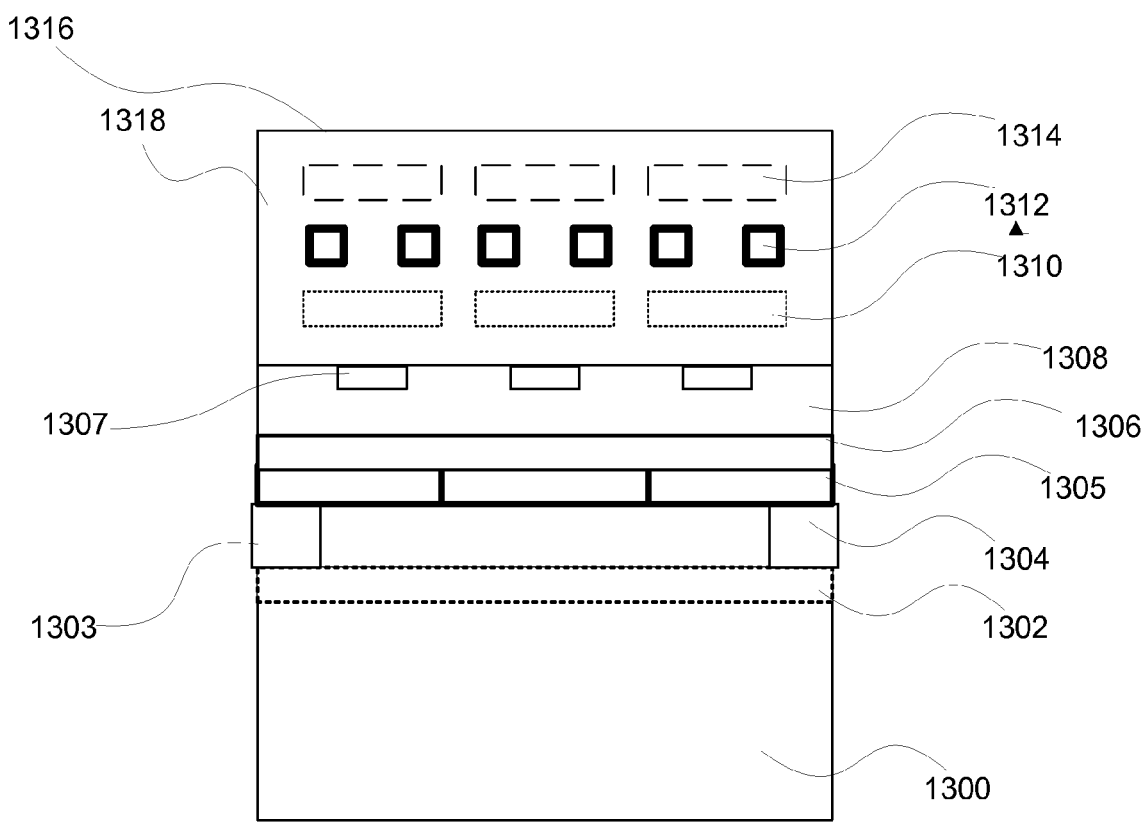
FIG. 13 is a diagram illustrating an embodiment of an integrated device with a Fabry-Perot etalon and an adjacent detector.

FIG. 13 is a diagram illustrating an embodiment of an integrated device with a Fabry-Perot etalon and an adjacent detector. In some embodiments, the integrated device of FIG. 13 is used to implement Fabry-Perot etalon 824 and detector 836 of FIG. 8. In the example shown, glass 1300 has thin metal coating 1302 separated from anti-reflective coating 1306 by spacer 1303 and spacer 1304 and spectral filters 1305. In various embodiments, spacer 1303 and spacer 1304 comprise static spacers, active spacers, Micro-Electro-Mechanical Systems (MEMS), piezoelectric movers, or any other appropriate spacers. Anti-reflective coating 1306 is coupled to silicon substrate 1308 with photodiodes 1307. Silicon substrate 1308 with photodiodes 1307 is coupled with silicon dioxide inter-metal dielectric 1318 with metal wires embedded (e.g., metal wires 1310, metal wires 1312 and metal wires 1314). The top comprises front side 1316 of the integrated device.

In some embodiments, an array of spectral (e.g., color) filters is deposited on the backside of the CIS wafer, such that the spectral response of different pixels changes. In some embodiments, the filter array is deposited between the Silicon wafer and the anti-reflection or metal-film layer. In some embodiments, the pattern density of the color filter array is higher than the spatial density of information to be collected from the object (i.e., the objects is spatially oversampled). In some embodiments, harmonics, which are an artifact of Fabry-Perot etalons, are resolved by oversampling the image on multiple pixels, each with a different filter and therefore a different spectral response, and thus the usable spectral range of the device is extended beyond its Free Spectral Range. In some embodiments, the color filter array is deposited on the glass plate and then passivated. In some embodiments, the color filter array is deposited on the flat, back surface of the wafer and not on the front surface. In some embodiments, a planarization layer is deposited on top of the color filter array—for example, in the form of low-temperature Chemical Vapor Deposition (CVD) or Physical Vapor Deposition (PVD) of $SiO_2$ and then planarized by chemical and/or mechanical polishing.

In some embodiments, Fabry-Perot interferometers have a limited spectral range, and so for these interferometers, the system includes two etalons in series—one in low finesse mode to select a band of wavelengths, and another in high finesse mode. In some embodiments, the BSI-CMOS etalon is the second one (e.g., the high finesse etalon) in this configuration.

In some embodiments, one or more MEMS wafers have dies of the same size as the BSI CMOS dies and comprises linear actuators (per die), which can adjust the spacing between the glass wafer and the BSI CMOS wafer. The MEMS wafer or a stack of MEMS wafers is placed in place of or in addition to the patterned spacer (e.g., as described above). Electrical contacts to enable adjustment of said spacing is achieved using either by direct access to the MEMS device (after the stack is diced) or by other means, such as but not limited to by electrical contact to through-silicon-vias (TSVs) on the CMOS BSI wafer.

In some embodiments, metallic capacitive elements are deposited on the surface of the glass plates of a Fabry-Perot etalon, and these are routed to a signal generator and measurement circuitry to monitor capacitance and therefore inter-plate separation. In various embodiments, a capacitive plate is deposited on the front glass plate and grounded, and a second capacitive plate is deposited on the CMOS front surface (just below the glass passivation) and connected—for example, using TSV's to capacitive measurement circuitry on the CMOS die, or connected using TSV's to a pad on the top surface of the die which is electrically connected to an off-chip capacitive measurement circuit, or in any other appropriate manner.

In various embodiments, either the glass wafer or the BSI CMOS wafer is bonded or otherwise coated with a patterned layer or layers (e.g., piezo-electric transducer), which, upon actuation with an electric field can change the separation between the glass and BSI wafers.

In some embodiments, a process flow for fabricating the device is as follows:
a CMOS BSI wafer is fabricated;
the CMOS BSI wafer is temporarily bonded on the front side to a carrier wafer;
the bonded CMOS BSI wafer is backgrinded such that the desired performance of the image sensor is achieved—for example, sufficiently thin to reduce cross-talk but not so thin as to reduce cross-talk or electrical performance.
through-Silicon-Vias (TSV) (e.g., using a "Via-Last" process) are formed on the periphery of each BSI CMOS die;
a piezoelectric transducer (e.g., PZT) pattern is formed or transferred on the CMOS BSI wafer such that the pattern is repeated for all dies, that the center of the die is free of the PZT, and that thickness of the piezoelectric material is on the order of a few to a few tens of microns. The piezoelectric material is electrically bonded to the TSVs on the CMOS BSI wafer. Alternately, this patterned piezoelectric transducer pattern may be formed or transferred on a second, glass or quartz wafer;
the glass and BSI CMOS wafer are bonded and diced to form Fabry-Perot etalon.

In some embodiments, the wafer spacer described above and the bonding of the two wafers is achieved using techniques. Several examples are as follows:
adhesive wafer bonding using photosensitive polymer layer. A polymer layer is spun on one of the wafers (preferably the glass wafer, photolithographically patterned, soft baked, aligned to the CMOS wafer, and bonded);
UV curable adhesives (UV curing via the glass wafer) or laser curable adhesives;
wafer-level camera module spacer attach process.

Figure 14:
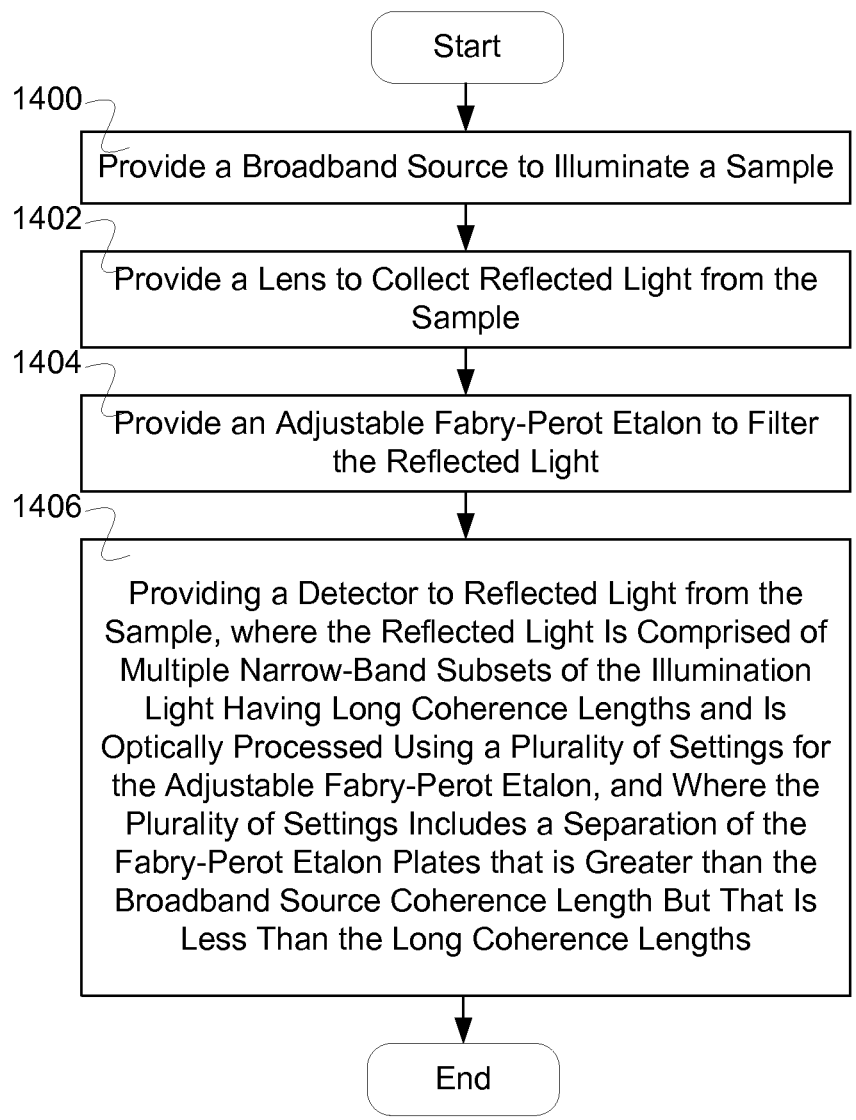
FIG. 14 is a flow diagram illustrating an embodiment of a process for making a relative spectral measurement.

FIG. 14 is a flow diagram illustrating an embodiment of a process for making a relative spectral measurement. In the example shown, in 1400 a broadband source is provided to illuminate a sample. For example, the one or more broadband sources provide illumination that is used to illuminate the sample and the one or more broadband sources have a short broadband source coherence length. In 1402, a lens is provided to collect reflected light from the sample. In 1404, an adjustable Fabry-Perot etalon is provided to filter the reflected light. For example, the adjustable Fabry-Perot etalon is to optically process the reflected light to extract spectral information with fine spectral resolution. In 1406, a detector is provided to detect reflected light from the sample, wherein the reflected light is comprised of multiple narrowband subsets of the illumination light having long coherence lengths and is optically processed using a plurality of settings for the adjustable Fabry-Perot etalon, and wherein the plurality of settings includes a separation of the Fabry-Perot etalon plates that is greater than the broadband source coherence length but that is less than the long coherence lengths. In some embodiments, the detector detects reflected light associated with a plurality of settings for the adjustable Fabry-Perot etalon, where the plurality of settings is without a setting of zero separation of the Fabry-Perot etalon plates.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for wide-range spectral measurement, comprising:
   one or more broadband sources to illuminate a rugate tag, wherein the one or more broadband sources have a short broadband source coherence length, wherein light from the one or more broadband sources is reflected by a beam splitter toward a lens to illuminate the rugate tag, wherein the light illuminates the rugate tag at a first angular cone, wherein the lens to collect reflected light from the rugate tag at a second angular cone, wherein the second angular cone is greater than the first angular cone;
   an adjustable Fabry-Perot etalon to optically process the reflected light to extract spectral information with fine spectral resolution;
   a detector to detect reflected light from the rugate tag, wherein the reflected light is comprised of multiple narrow-band subsets of the illumination light having long coherence lengths and is optically processed using a plurality of settings for the adjustable Fabry-Perot etalon, and wherein the plurality of settings includes a separation of the Fabry-Perot etalon plates that is greater than the broadband source coherence length but that is less than the long coherence lengths; and
   a processor configured to determine if the detected reflected light from the rugate tag displays a predetermined reflectivity spectrum associated with the rugate tag.

2. A system as in claim 1, wherein the reflected light is imaged on to the adjustable Fabry-Perot etalon.

3. A system as in claim 1, wherein the adjustable Fabry-Perot etalon is set at a first separation distance to measure a response at a first wavelength.

4. A system as in claim 3, wherein the adjustable Fabry-Perot etalon is set at a second separation distance to measure a response at a second wavelength.

5. A system as in claim 1, wherein the optically processed reflected light is imaged on to the detector.

6. A system as in claim 1, wherein the adjustable Fabry-Perot etalon is separated from the detector by imaging optics.

7. A system as in claim 6, wherein the imaging optics comprise one or more lenses.

8. A system as in claim 1, wherein the adjustable Fabry-Perot etalon and the detector are combined in an integrated device.

9. A system as in claim 8, wherein the integrated device comprises a backside imaging sensor.

10. A system as in claim 8, wherein the integrated device comprises a Fabry-Perot etalon.

11. A system as in claim 8, wherein the integrated device comprises one or more movers.

12. A system as in claim 8, wherein a mover of the one or more movers comprises a MEMS mover.

13. A system as in claim 8, wherein a mover of the one or more movers comprises a piezoelectric mover.

14. A system as in claim 1, wherein the rugate tag, the Fabry-Perot etalon, and the detector are telecentric.

15. A system as in claim 1, wherein the rugate tag contains a complex porous nanostructure that is programmed during electrochemical synthesis to display the predetermined reflexivity spectrum.

16. A method of relative spectral measurement, comprising:
   providing one or more broadband sources to illuminate a rugate tag, wherein the one or more broadband sources have a short broadband source coherence length, wherein light from the one or more broadband sources is reflected by a beam splitter toward a lens to illuminate the rugate tag, wherein the light illuminates the rugate tag at a first angular cone, wherein the lens to collect reflected light from the rugate tag at a second angular cone, wherein the second angular cone is greater than the first angular cone;
   providing an adjustable Fabry-Perot etalon to optically process the reflected light to extract spectral information with fine spectral resolution;
   providing a detector to detect reflected light from the rugate tag, wherein the reflected light is comprised of multiple narrow-band subsets of the illumination light having long coherence lengths and is optically processed using a plurality of settings for the adjustable Fabry-Perot etalon, and wherein the plurality of settings includes a separation of the Fabry-Perot etalon plates that is greater than the broadband source coherence length but that is less than the long coherence lengths; and
   determining, using a processor, whether the detected reflected light from the rugate tag displays a predetermined reflectivity spectrum associated with the rugate tag.

* * * * *